United States Patent [19]

Moore

[11] 4,349,917
[45] Sep. 14, 1982

[54] TOMOGRAPHIC METHOD AND APPARATUS

[75] Inventor: Robert M. Moore, Midlothian, Va.

[73] Assignee: Kermath Manufacturing Corporation, Richmond, Va.

[21] Appl. No.: 157,602

[22] Filed: Jun. 9, 1980

Related U.S. Application Data

[63] Continuation of Ser. No. 963,704, Nov. 24, 1978, abandoned.

[51] Int. Cl.$^3$ ............................................. G03B 41/16
[52] U.S. Cl. ..................................... 378/24; 378/27; 378/164
[58] Field of Search ........................... 250/445 T, 476

[56] References Cited

U.S. PATENT DOCUMENTS 3,973,127  8/1976  Matsuda .......................... 250/445 T
4,174,481  11/1979  Liebetruth ....................... 250/445 T Primary Examiner—Craig E. Church
Attorney, Agent, or Firm—Griffin, Branigan & Butler

[57] ABSTRACT

A tomographic x-ray machine has camera and film-plane sections which move about a primary axis for imaging a selected cross-section of an anatomical member onto a film. A "scout image" of the member is obtained at right angles to the plane of the desired cross-section to indicate the cross-section's orientation with respect to the primary axis. The anatomical member is then moved to place it on the primary axis and a second film is located at the same angle that the selected cross-section makes with the primary axis. The second film and the cross-section are then maintained in parallel planes throughout motion of the camera and the second film during tomographic radiography.

19 Claims, 10 Drawing Figures

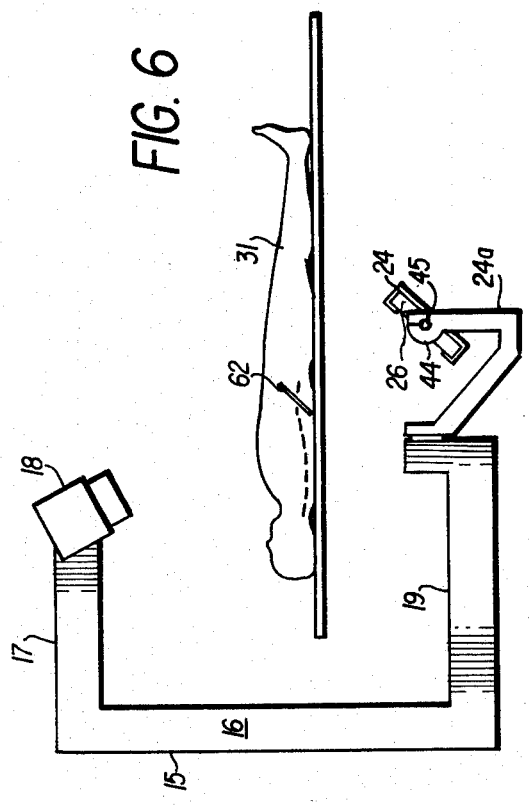
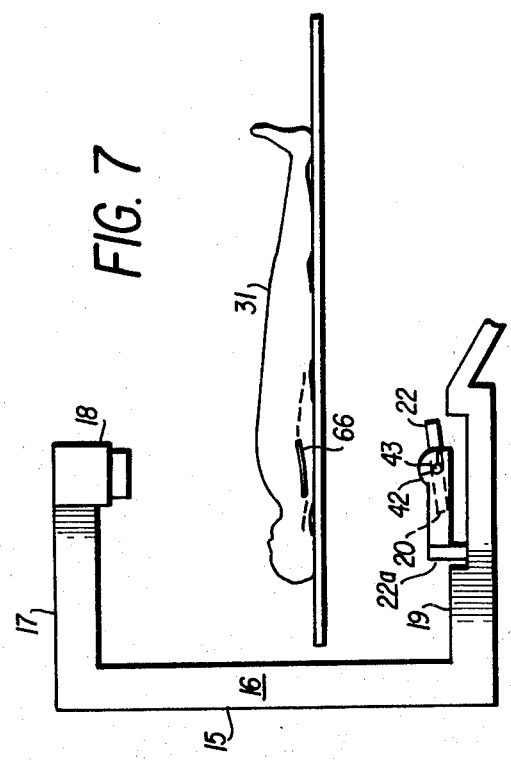
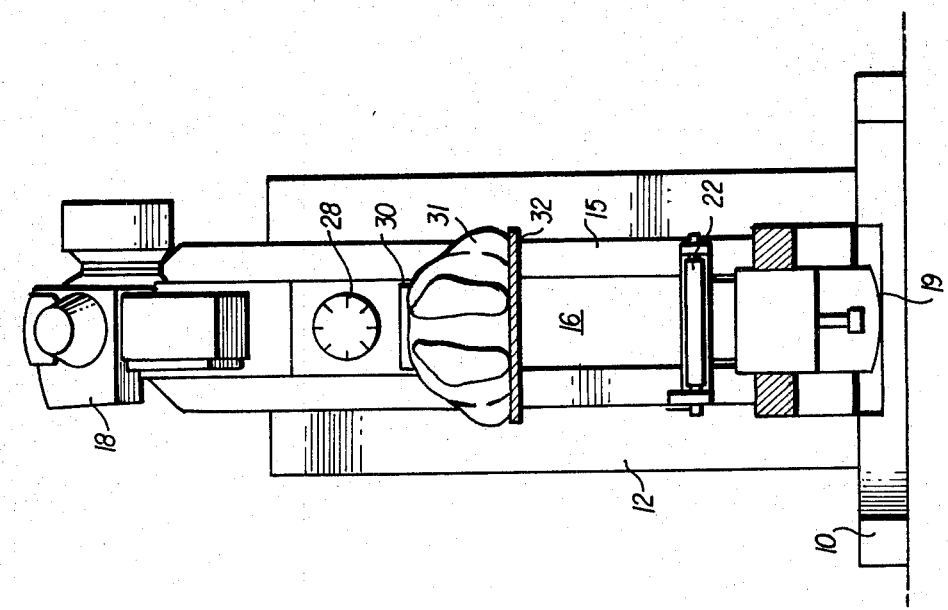

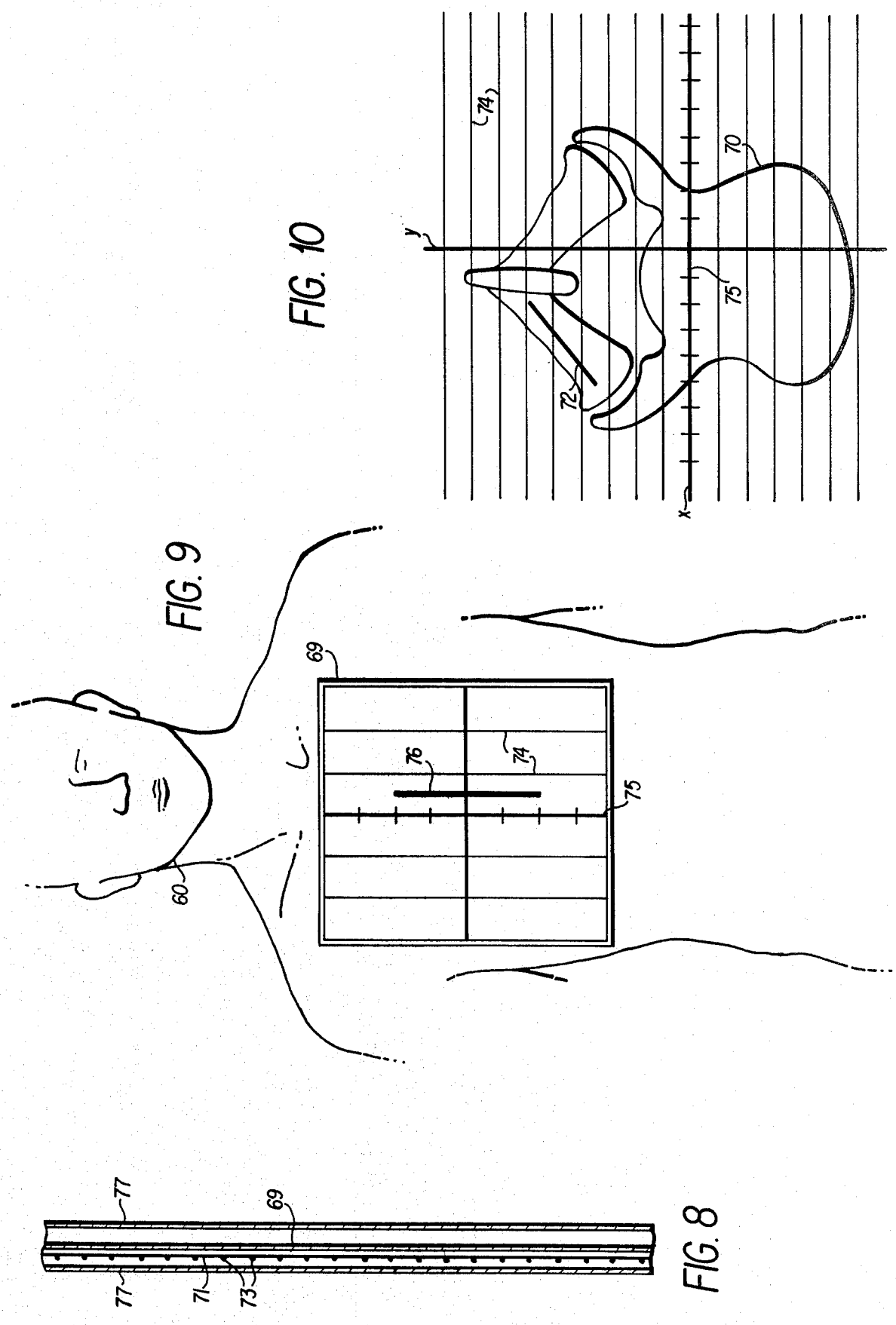

TOMOGRAPHIC METHOD AND APPARATUS

This is a continuation of application Ser. No. 963,704, filed 11/24/78, now abandoned.

BACKGROUND OF THE INVENTION

Tomography is a radiological technique which provides a readable image of a plane through a human body while the images of the body structures that lie above and below that plane are blurred. Tomographic images are obtained by a special mechanism that moves an x-ray camera and x-ray film in a manner so that the center of the x-ray beam is always aligned with the center of the film. The x-ray camera and the film rotate, for example, about a center of rotation which lies on the plane to be imaged within the body. In this respect, the x-ray camera and the film describe arcs about the center of rotation, but the plane of the film's surface remains oriented in a position parallel to the plane to be imaged within the body as the film moves in its arc. Thus the plane that passes through the center of rotation and is parallel to the film is recorded on the same area of the film irrespective of the changing position of the x-ray camera; and, the image of the selected plane is thereby distinctly recorded on the film. The images of structures above and below the desired plane, however, are recorded in a series of positions on the film and appear blurred.

Although tomography as described provides the doctor with a capability of taking a look at a cross-sectional slice across the human body, there may be an excessive amount of distortion if the imaging plane through the body is not a true perpendicular or parallel slice through the body member being examined. Thus a circular member may appear in the image as an ellipse and, therefore, cannot be measured accurately. It is a purpose of this invention, therefore, to provide a method and an apparatus whereby cross-sectional views are not only in focus, but can be put in proper perspective and size correctly and without distortion.

Tomographic slices are normally only between 1 to 10 millimeters in thickness. Hence in a large anatomical member a relatively small error in the angle of the film results in an image of only a small portion of the desired slice. Moreover, when the desired slice is missed by the tomographic x-ray because of an incorrect angle, it will very likely go undetected. It is a purpose of this invention, therefore, to provide a method and apparatus whereby a determination can be made of the angle at which an anatomical member should be x-rayed.

Current techniques often necessitate repeated trial-and-error tomographic x-rays to obtain the desired image. The patient, therefore, is exposed to large doses of radiation. Accordingly, it is another purpose of this invention to reduce the patient's exposure to radiation.

An additional advantage of the invention is that prior x-rays can be accurately and easily repeated at a later date (such as after surgery) without again subjecting the patient to additional trial-and-error doses of radiation.

Another problem with tomography is that the mechanisms are so large and bulky that they can't be conveniently moved or repositioned. Hence, the patient must often be physically moved to obtain the desired, angled slices. Consequently, the victim of an accident with a broken neck or other bones may be further injured in the movement or adjustment needed to obtain a cross-sectional tomographic x-ray of the damaged area. In this respect, an additional advantage of this invention is that a patient can be placed in a prone position on a table, for example, and all tomographic x-rays can be taken without having to move the patient, while, at the same time obtaining undistorted cross-sectional images of desired areas.

SUMMARY

The actual position of the anatomical member of which a sectional image is desired is determined by means of a "scout image." The angle of the selected portion of the desired member is then determined from the scout image which is shot along an axis that is parallel to the desired plane within a given member. The film cassette is then angled accordingly so that it is parallel to the plane of the desired cross-section. Thereafter, the U-frame on which the camera and the film cassette holder are mounted can be moved with respect to the table on which the patient is positioned thus precluding the need to move an injured patient.

BRIEF DESCRIPTION OF THE DRAWINGS

The foregoing and other objects, features, and advantages of the invention will be apparent from the following more particular description of preferred embodiments of the invention as illustrated in the accompanying drawings, wherein the same reference characters refer to the same parts throughout the various views. The drawings are not necessarily drawn to scale. Instead, they are merely presented so as to illustrate principles of the invention in a clear manner.

FIG. 3 is a schematic view of the FIG. 1 unit taken along the lines 3—3 thereof.

FIG. 6 is a schematic side-view of the FIG. 4 structure, but with the film cassette angled for a transverse axial tomograph of a non-horizontal portion of the spine.

FIG. 7 is a schematic illustration of a patient in the base position, but with the normally horizontal film cassette angled for an AP linear tomograph of a non-horizontal portion of the spine.

FIG. 8 is a schematic cross-section of a portion of a radiographic film cassette including a scout grid.

FIG. 9 is a schematic illustration including a scout film having a scout grid.

FIG. 10 is a schematic illustration of a vertebrae as it would appear on a transverse axial tomographic scout film.

DETAILED DESCRIPTION

Figure 1:
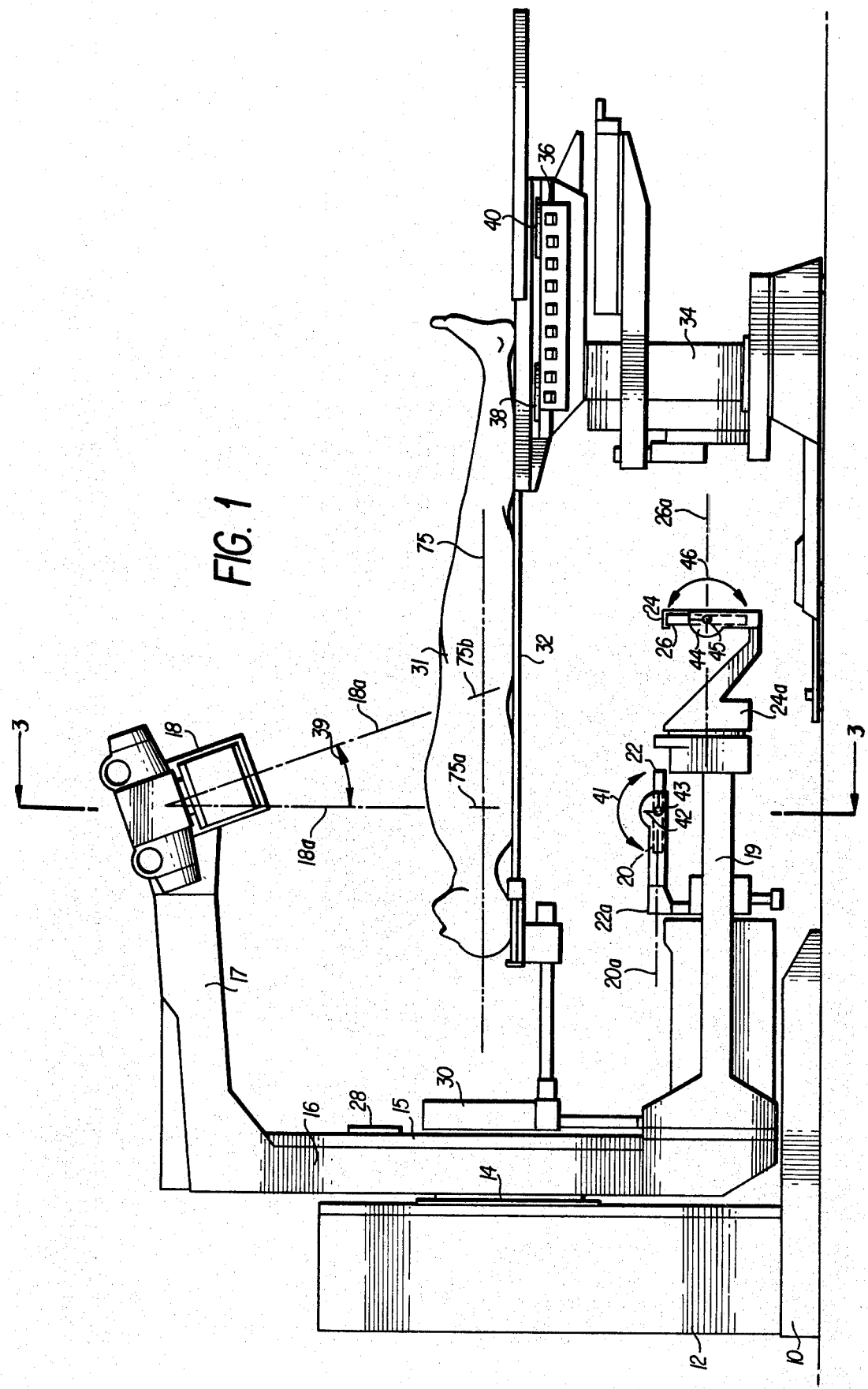
FIG. 1 is a side view of an x-ray unit in a base position.
Figure 2:
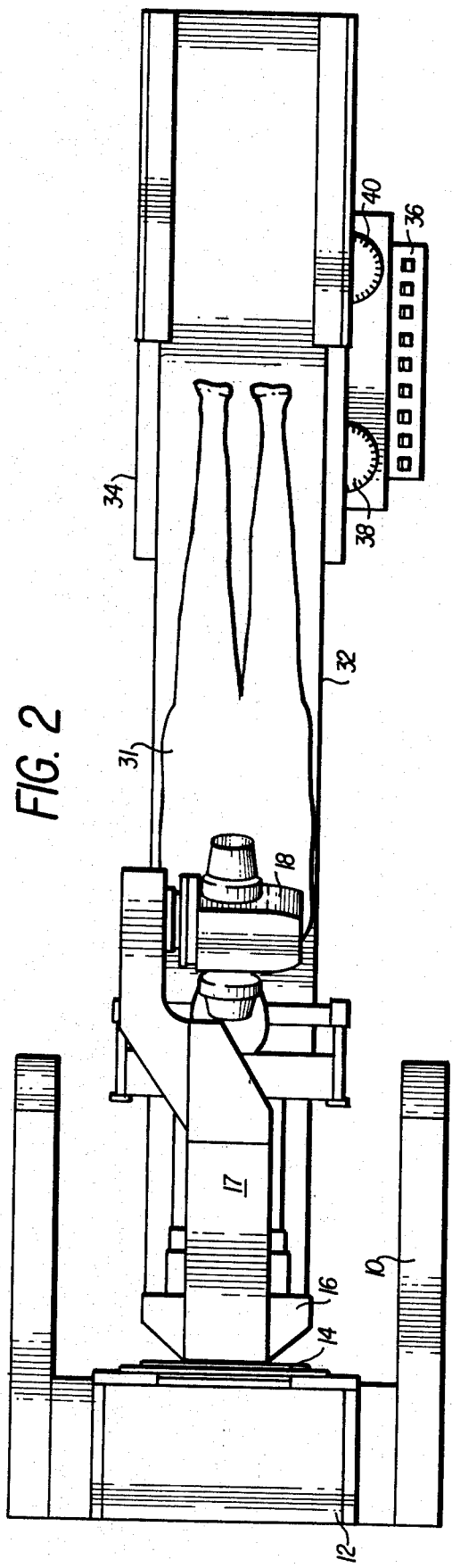
FIG. 2 is a top view of an x-ray unit in a base position.

The tomographic x-ray equipment illustrated in FIG. 1 is largely within the current state of the art. It has a base plate 10 which supports a pedestal 12 containing controls, gearing, and pivot support mechanisms 14 for the tomographic system. A structural U-frame 16 is mounted at its cross-bar 15 on the pivot support 14 of the pedestal 12. On one of the U-frame's arms 17 is mounted an x-ray camera 18, and on the end of the other arm 19 are mounted a holder 20 for an "LT"

(linear tomography) cassette 22 and a holder 24 for a "TAT" (transverse axial tomography) cassette 26.

Mounted on the inside of the cross-member 15 are an elevator scale 30 and a rotation scale 28.

A patient 31 lies on a table top 32 which is supported by a mobile table-base 34. Mounted on the side of the mobile table-base 34 is a motion control panel 36, a longitudinal adjustment scale 38 for the table top, and a lateral adjustment scale 40 for the table top.

As indicated by arrow 39, the x-ray camera 18 can be adjusted to focus on either the LT cassette 22 or the TAT cassette 26.

As indicated by the arrows 41 on FIG. 1 the LT cassette holder 20 is pivotable from the horizontal position about pivot pins 43 at its midpoint and locked or held by split clamps in a desired position at an angle with the horizontal as indicated by a vernier scale 42 or the like. Similarly, as indicated by arrow 46, the TAT cassette holder 24 is pivotable from the vertical position about pivot pins 45 at its midpoint and locked or held by split clamps in a desired position at a selected angle with the vertical as indicated by a vernier scale 44.

The center lines of the pivot pins on both cassette holders 20 and 26 are located in the plane of the x-ray film in the respective cassettes, and, preferably on secondary axes of rotation 20a and 26a, respectively.

As the U-frame 16 is rotated about the pivot 14, the x-ray camera 18 and the cassette holders 20 and 24 move in arcs about the pivot 14 located on the machine's primary axis of motion. As the cassette holders 20 and 24 move through such arcs, they are maintained parallel to an initial desired position through suitable drive mechanisms.

Figure 5:
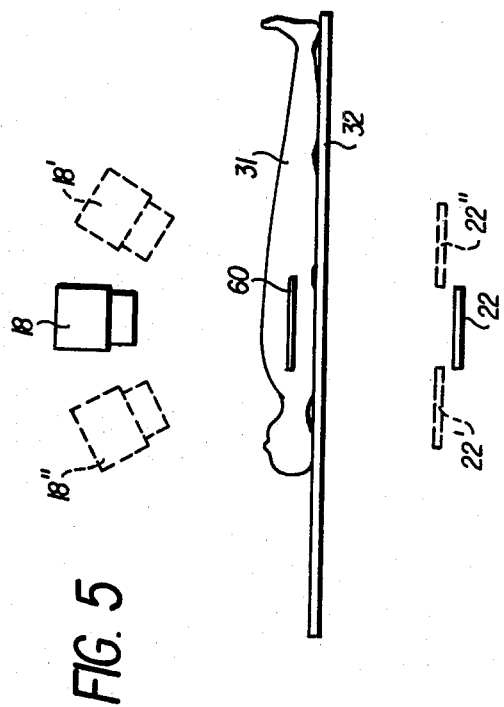
FIG. 5 is a schematic end-view of a unit similar to that of FIG. 2, but with the table rotated 90 degrees and the unit in an "AP" linear tomographic position.
Figure 4:
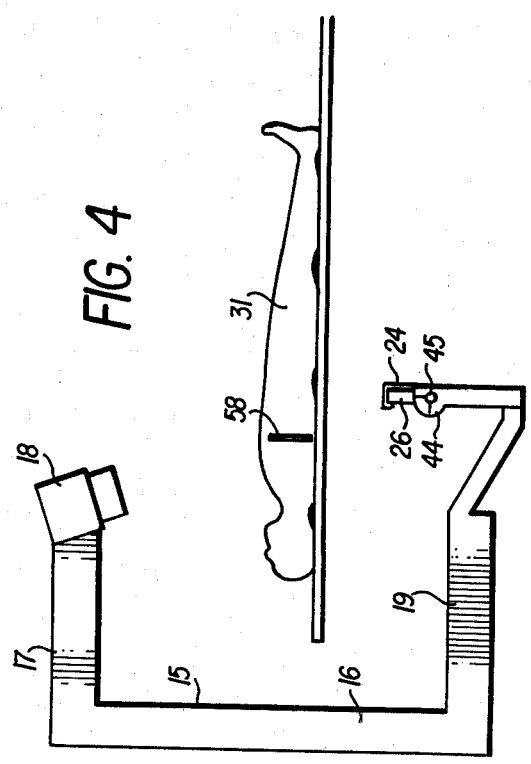
FIG. 4 is a schematic side-view of an x-ray unit in a transverse axial tomographic position.

Cross-sectional slices of which tomographic images may be taken, for example, are a vertical transverse axial slice 58 taken with the unit in the TAT (transverse axial tomographic) position (FIG. 4) or a horizontal slice 60 taken with the unit in the AP LT (anterior-posterior linear tomographic) position with the table rotated into the position illustrated in FIG. 5.

Other horizontal, oblique, and lateral slices, among others, can also be taken, but they are within the state of the art and are not illustrated herein.

In operation a first x-ray is first taken of the anatomical member of which tomographic x-rays are desired. These first x-rays, designated "scout films" 69 are taken through an acetate screen 71 (FIG. 8) with silk-screen grid lines 73 overlaying the film to block out illumination from illuminating screens 75 and provide a scaled grid 74 on the film when developed as indicated in FIG. 9. The grid scale 74 is proportioned at the same fixed magnification as the system and correlates with the measurements on the elevator scale 30, the longitudinal adjustment scale 38 and the lateral adjustment scale 40. As can be seen in FIG. 9, the centimeter scale of the grid 74 indicates the movement needed on the lateral adjustment scale 40 to position the tomographic slice 76 on the primary axis of rotation 75 of the U-frame 16.

A first scout film is taken along an axis that is parallel to the plane of the anatomical cross-sectional slice of which a tomographic image is desired. In this respect, the scout film is perpendicular to the plane of the desired cross section. The angle which the desired plane-to-be-imaged makes with either the vertical or horizontal axis is then accurately measured from the first scout film; and, the angle of the TAT film cassette 26 as indicated by the vernier 44, or the LT film cassette 22 as indicated by the vernier 42 is pivoted and clamped in position about pivots 43 or 45 to align the cassettes 22 or 26 in a plane parallel to the selected plane-to-be-imaged.

The distance that the centerpoint of the desired plane-to-be-imaged is removed from the axis of rotation of the U-frame 16 and from the centerline of the x-ray beam may be measured from the scout film and the table top or the height of the pivot 14 may be adjusted accordingly.

A second scout film may be taken from an angle perpendicular to the plane of the cross-sectional slices to provide measurements for positioning the table 32 or elevating the pivot 14.

From the scout film, the center of the axis of the plane of the anatomical cross-sectional slice can be determined, and it can then be accurately moved to be positioned on the primary axis of rotation of the U-frame 16 and the camera-cassette focal line (x-ray beam) by elevating the pivot 14 or by making lateral adjustment of the table top 32. The longitudinal position of the table is then used to adjust to the centerline of the x-ray beam.

Scout film may be taken from an anterior-posterior (AP) position, a lateral position, or a TAT position. A precise TAT scout film may be made using measurements from AP or lateral scout films and then used to position one finite element of an anatomical member and the corresponding cassette for an accurate tomographic x-ray. A TAT scout film illustrated in FIG. 10 was made to determine the angle at which to position the LT cassette parallel the desired tomographic slice 72 of a vertebrae 70. Grid lines 74 indicated in centimeters (but actually spaced apart in accordance with the machine's magnification) indicate the movement needed to place the center of the cross-sectional tomographic slice 72 of the vertebrae on the primary axis of motion 75 of U-frame 16. The distance between center of slice 72 and the axis y in FIG. 10 corresponds to the distance the table must be moved laterally to align the center of slice 72 with the center of the x-ray beam (18a in FIG. 1). The table is also moved by the fixed distance between 75a and 75b in FIG. 1 in order to shift from one mode such as LT to the other such as TAT. In this respect, since the distance between 75a and 75b is fixed, scout films taken in one mode can be used to locate the slice in the other mode.

The machine is then set up so that the film plane is parallel to the desired slice and centered on the main x-ray beam for the production of otherwise conventional tomographic x-rays as indicated in FIGS. 4 through 7. In this respect, in the situation described in connection with FIG. 10, instead of angling the LT cassette 22, the U-frame 16 is rotated so that the center of the x-ray beam is perpendicular to the slice 72.

A precise vertical cross-sectional slice 62 is indicated in FIG. 6 with the film cassette 26 angled to parallel the plane of the slice 62. The vernier scale 44 mounted on TAT cassette holder arm 24a indicates the vertical alignment of the TAT film cassette holder 24 which is brought into parallelism with the plane of the selected cross-sectional slice 62. Similarly, an accurate slice 66 is indicated in FIG. 7 with the LT cassette holder 20 brought into parallelism with the plane of the selected slice 66. In this respect, the vernier scale 42 mounted on the LT cassette-holder arm 22a measures the angle of the LT film cassette holder 20 and its cassette 22 to indicate their parallelism with the non-horizontal plane of the slice 66.

It can be readily seen from the above described structure that both standard radiographs and tomographs can be taken from almost every conceivable angle without having to move the patient. This is accomplished by using scout films to help the radiologist and the doctor accurately define the position of the body member of which the tomographic slice or layer is desired. The body member and the x-ray film can then be accurately positioned with respect to each other so that the resulting image obtained is the selected slice desired and the image is both clear and undistorted. In this manner accurate measurements can be taken for use in connection with subsequent treatment in surgery. In this regard the structure of the invention provides the ability to have the plane of the x-ray film angled so that it parallels or accurately corresponds to the selected cross-section of the anatomical area of interest. This overcomes the distortion and inaccuracies which are prevalent in the current state-of-the-art units which are restricted to a plane which is generally parallel to or vertical to an x-ray table top. Additionally, the structure of the invention provides for accurate motion of a cassette to align the film with the desired slice through an imobile patient—as opposed to undesirable and inaccurate movement of the patient to bring the slice into alignment with a fixed cassette.

It should be understood that while the above-described preferred embodiments gives specific details, modifications will be available to those knowledgeable in the art. The invention, has been described, for example, in connection with a TAT and Linear machine, but it is also applicable to pluridirectional machines capable of shooting a scout film at right angles to the desired tomographic slice.

The embodiments of the invention in which an exclusive property or privilege is claimed are defined as follows:

1. Tomographic radiological apparatus having an x-ray source, an object support and a film holder for providing an image of a selected cross-section of a given object, said apparatus further comprising:
   means for recording reference data on a first film within a holder, said reference data indicating the location of the object relative to the apparatus;
   means for accurately positioning said selected cross-section of said object with respect to an x-ray beam from said source and a primary axis of rotation about said object by said x-ray source and a second film;
   means for accurately locating said second film with respect to said reference-data so as to be in a plane parallel to the plane of said selected cross-section; and,
   means to move said x-ray source and said second film with respect to said primary axis of rotation while maintaining parallelism between said second film and said selected cross-section so as to image said selected cross-section at said second film during such motion.

2. Apparatus of claim 1 wherein said means for accurately positioning said selected cross-section includes means for obtaining relative motion between said primary axis of rotation and said selected cross-section so that said primary axis of rotation passes through the center of said selected cross-section.

3. Apparatus of claim 1 wherein said means for recording reference data on said first film includes grid lines to be imaged on said first film.

4. Apparatus of claim 3 wherein said grid lines are imaged onto said first film by means of an overlay for blocking radiation from said x-ray source from striking selected portions of said first film.

5. Apparatus of claim 3 wherein said means for recording reference data includes illumination-screen means.

6. Apparatus of claim 5 wherein said grid lines are imaged onto said first film by means of an overlay located between an illumination screen and said first film for blocking illumination from said illumination screen from striking said portions of said first film.

7. Apparatus of either claim 4 or 6 wherein said overlay is comprised of an acetate screen having grid lines thereon.

8. Apparatus of claim 3 wherein said grid lines are spaced apart from each other in proportion to the magnification of the image of said object on said first film.

9. Apparatus of claim 1 wherein said reference data is recorded on said first film in a plane perpendicular to the plane of said selected cross-section.

10. Apparatus of claim 1 wherein said means for accurately locating said second film includes:
   cassette means for holding said second film;
   means for pivotally mounting said cassette and thereby said second film for motion about an axis perpendicular to said primary axis of rotation; and,
   means for holding said cassette and thereby said second film in a selected plane for receiving radiation from said x-ray source.

11. Apparatus of claim 10 including means for moving said cassette about an axis parallel to said primary axis of rotation.

12. A method of using tomographic radiological apparatus for providing a tomographic radiological image of a selected cross-section of a given object wherein said selected cross-section is imaged by an x-ray source upon film, said method comprising the steps of:
   recording reference data on a first film, said reference data indicating the location of the object relative to the apparatus;
   accurately positioning said selected cross-section of said object with respect to an x-ray beam from said source and a primary axis of rotation of said x-ray source about said object;
   accurately locating a second film with respect to said reference-data so as to be in a plane parallel to the plane of said selected cross-section; and,
   moving said x-ray source and said second film with respect to said primary axis of rotation while maintaining parallelism between said second film and said selected cross-section so as to image said selected cross-section on said second film during such motion.

13. The method of claim 12 wherein said step of positioning said selected cross-section includes the step of relatively locating said selected cross-section and said primary axis of rotation so that said primary axis of rotation passes through the center of said selected cross-section.

14. The method of claim 12 wherein said step of recording reference-data on said first film includes the step of imaging grid lines thereon.

15. The method of claim 14 wherein said grid line images are spaced-apart from each other in proportion to the magnification of the image of said object on said first film.

16. The method of claim 12 wherein said first film is located perpendicular to the plane of said selected cross-section.

17. The method of claim 12 wherein said step of accurately locating said second film includes the steps of pivoting said second film about an axis that is perpendicular to said primary axis and then holding said second film in the desired plane parallel to said selected cross-section during said motion of said second film about said primary axis.

18. The method of claim 17 including the step of pivoting said second film about an axis parallel to said primary axis prior to said motion of said second film about said primary axis.

19. The method of claim 12 wherein said reference-data is recorded tomographically.

* * * * *